United States Patent
Cherian

(10) Patent No.: US 6,287,593 B2
(45) Date of Patent: *Sep. 11, 2001

(54) LIPID COMPLEXES AND LIPOSOMES OF HIGHLY INSOLUBLE PLATINUM COMPLEXES

(75) Inventor: Mathew Cherian, Arese (IT)

(73) Assignee: Pharmacia & Upjohn, Milan (IT)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/341,988

(22) PCT Filed: Jan. 28, 1998

(86) PCT No.: PCT/US98/00035

§ 371 Date: Jul. 21, 1999

§ 102(e) Date: Jul. 21, 1999

(87) PCT Pub. No.: WO98/33481

PCT Pub. Date: Aug. 6, 1998

Related U.S. Application Data

(60) Provisional application No. 60/037,377, filed on Feb. 5, 1997.

(51) Int. Cl.$^7$ .................................................. A61K 9/127
(52) U.S. Cl. ............................ 424/450; 514/492; 264/4.1; 264/4.3
(58) Field of Search .................................. 424/450, 649; 514/492; 264/4.1, 4.3

(56) References Cited

U.S. PATENT DOCUMENTS

| | | | | |
|---|---|---|---|---|
| 4,927,571 | * | 5/1990 | Huang | .................................. 264/4.3 |
| 5,384,127 | * | 1/1995 | Perez-Solen | ........................ 426/450 |
| 5,393,909 | | 2/1995 | Khokhar et al. . | |
| 5,843,475 | * | 12/1998 | Perez-Solen | ......................... 424/450 |

FOREIGN PATENT DOCUMENTS

| | | |
|---|---|---|
| 0 113 508 | 7/1984 | (EP) . |
| 0 356 332 | 2/1990 | (EP) . |
| 03 200 795 | 9/1991 | (JP) . |

* cited by examiner

*Primary Examiner*—Gollamudi S. Kishore
(74) *Attorney, Agent, or Firm*—McDonnell Boehnen Hulbert & Berghoff

(57) ABSTRACT

A pharmaceutical composition comprising a lipid complex or a liposome of a phospholipid and a water-insoluble platinum dicarboxylate and method for the preparation of such compositions are described.

14 Claims, No Drawings

LIPID COMPLEXES AND LIPOSOMES OF HIGHLY INSOLUBLE PLATINUM COMPLEXES

This application is a 371 of PCT/US98/00035, filed Jan. 28, 1998, which claims the benefit of U.S. provisional application 60/037,377, filed Feb. 5, 1997.

The present invention relates to a lipid complex or liposome of highly insoluble platinum complexes, and more particularly to a phospholipid complex of a platinum dicarboxylate which can be reconstituted in a pharmaceutically acceptable vehicle with or without lyophilization and administered to a patient in the treatment of cancer and other diseases.

Several platinum complexes have shown excellent activity against cancer. The clinical use of such complexes has been severely limited by the insolubility of the complexes in pharmaceutically acceptable vehicles. For example, diaminocyclohexane (DACH) complexes with platinum compounds have been shown to be active against several types of cancer. However, the DACH-Pt complexes are quite insoluble in aqueous vehicles and many organic solvents. The insolubility of the DACH-Pt in organic solvents has precluded their encapsulation in liposomes or their use in lipid complexes by known methods.

Accordingly, there is a need for a solubilized, pharmaceutically stable form of the highly insoluble moieties such as DACH-Pt complexes.

SUMMARY OF THE INVENTION

It is an object of the present invention to provide a soluble, pharmaceutically acceptable dosage form of water-insoluble platinum complexes.

It is another object of the invention to provide phospholipid complexes or liposomes of diaminocyclohexane-platinum complexes.

It is still another object of the invention to provide a lyophilized pharmaceutically acceptable dosage form of diaminocyclohexane-platinum-phospholipid complexes or liposomes.

While the invention will hereafter be described with respect to the preparation of lipid complexes or liposomes of diaminocyclohexane-platinum malonate and lyophilizates of lipid complexes of diaminocyclohexane-platinum malonate, those skilled in the art will appreciate that the methods taught herein are also applicable to the preparation of lipid complexes or liposomes and lyophilizates of other platinum complexes which are considered water-insoluble and cannot be administered by injection or infusion.

In accordance with a specific embodiment of the present invention, phospholipid complexes or liposomes of a diaminocyclohexane-platinum dicarboxylate which can be reconstituted with a pharmaceutically acceptable aqueous diluent such as water for injection are provided.

The soluble phospholipid complex of the DACH-platinum dicarboxylate is prepared in situ by a method which comprises reacting DACH with potassium tetrachloroplatinate and potassium iodide to form DACH-platinum iodide followed by reacting the DACH-platinum iodide with silver nitrate to yield DACH-platinum nitrate. The DACH-platinum nitrate is then simultaneously reacted with a phospholipid in a chloroform/ethanol solution and a carboxylic acid to form the lipid complex of DACH-platinum dicarboxylate product. It has been found that carboxylation of the platinum complex greatly reduces its water solubility. In accordance with the invention, by postponing carboxylation until formation of the lipid complex or liposome, the solubility of the platinum entity is maintained so that a solution of the complex is available for formation of the lipid complex or liposome.

The DACH-Pt-dicarboxylates of the present invention can also be prepared as liposomes. Liposomes are widely described in the literature and their structure is well known. In the present invention, liposomes are made by forming a film of the active ingredient, in this case DACH-Pt nitrate and the phospholipid, adding a carboxylic acid, and evaporating the solvent for the phospholipid, e.g., chloroform/ethanol to form the film, adding water for injection, and finally homogenizing the formed liposome.

DETAILED DESCRIPTION OF THE INVENTION

The term "lipid complex" is an art recognized term in the preparation of pharmaceutical compounds. Lipid complexes are characterized by a non-covalent bond between the lipid and the pharmaceutical compound which is observed as a phase change in differential scanning calorimetry.

The term "pharmaceutically acceptable aqueous diluent" as used herein refers to water for injection, saline, and other known aqueous vehicles.

The term "lyophilization excipient" refers to a substance which is added to a solution prior to lyophilization to enhance characteristics such as the color, texture, strength, and volume of the cake. Examples of lyophilization excipients are provided below.

In accordance with one embodiment of the present invention, the lipid complexes of diaminocyclohexane platinum complexes are prepared according to the following reaction scheme:

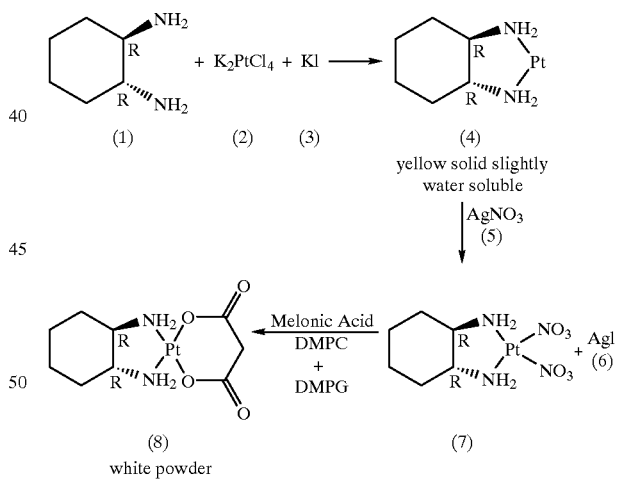

As illustrated in the first step above, diaminocyclohexane (1), potassium tetrachlor-palatinate (2) and potassium iodide (3) in stoichiometric amounts are reacted together in water to yield diaminocyclohexane-platinum iodide (4) which is only slightly soluble in water. Silver nitrate solution (5) is added to the diaminocyclohexane-platinum iodide (3) to form diaminocyclohexane-platinum nitrate (6). The diaminocyclohexane-platinum nitrate (6) is water soluble but is not useful as an anti-neoplastic agent because of its nephrotoxic properties. The appropriate phospholipid (7), preferably, a mixture of dimyristoyl phosphatidyl choline and dimyristoyl phosphatidyl glycerol, in a chloroform/ ethanol solution is added to the daiminacyclohexane-platinum nitrate (6) simultaneously with an excess of a dicarboxylic acid (8) such as malonic acid (illustrated here). Upon removal of the chloroform/ethanol solvent by sparging with nitrogen, the diaminocyclohexane-platinum dicarboxylate (9) is formed which is, at the same time, complexed with the phospholipid (7). The diaminocyclohexane-platinum dicarboxylate product (9) is then centrifuged and resuspended in water for injection. While the above procedure is directed to preparing DACH complexes, those skilled in the art will recognize that other ligands or chelating agents can be used to provide other complexes.

The carboxylic acids useful in the present invention to prepare the diaminocyclohexane-platinum dicarboxylates include oxalic acid, malonic acid, succinic acid, glutaric acid, adipic acid, pimelic acid, maleic acid, fumaric acid, azelaic acid, suberic acid, sebasic acid, tartaric acid, phthalic acid, and the like. The acid may be substituted or unsubstituted. In a preferred aspect of the invention, malonic acid is the acid of choice.

The diaminocyclohexane platinum-dicarboxylates useful in the present invention have the following structure:

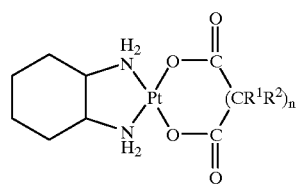

where $R^1$ and $R^2$ are the same or different and represent, hydrogen, $C_1$–$C_{10}$ alkyl $C_6$–$C_{10}$ aryl, $C_7$–$C_{18}$ alkaryl, $C_7$–$C_{18}$ aralkyl, or $R^1$ and $R^2$ may form a substituted or unsubstituted, saturated or unsaturated, 4,5, or 6-member ring; or $R^1$ or $R^2$ may combine with $R^1$ or $R^2$ on an adjacent carbon atom to form a substituted or unsubstituted, saturated or unsaturated 4, 5, or 6-member ring; and n is 0–10.

Typically the diaminocyclohexane-platinum carboxylate is diaminocyclohexane-platinum oxalate, diaminocyclohexane-platinum malonate, diaminocyclohexane-platinum succinate, diaminocyclohexane-platinum glutarate, diaminocyclohexane-platinum adipate, diaminocyclohexane-platinum pimelate, diaminocyclohexane-platinum maleate, daiminocylclohexane-platinum fumerate, diaminocyclohexane-platinum phthalate, and diaminocyclohexane-platinum tartrate. Preferably, the diaminocyclohexane-platinum dicarboxylate is diaminocyclohexane-platinum malonate or a diaminocyclohexane-platinum malonate in which the malonate is substituted with, e.g., and alkyl group or the like such as a butyl group.

The organic solvent used to prepare the solution of the phospholipids must be compatible with the phospholipids and not destabilize them or the DACH-Pt nitrate complex. In addition, the lipids should be soluble enough in the solvent so as to be able to introduce enough of the lipid to form the complex yet minimize the amount of solvent that must be removed later. A volatile or low boiling solvent which can be readily removed from the dispersion of the lipid complex is most preferred. The solvent most typically used to prepare this solution is chloroform, ethanol or methylene chloride or mixtures thereof. A mixture of chloroform and ethanol provides good results in the present invention.

Phospholipids are amphipathic in nature, i.e., the molecules have a hydrophobic tail such as a long chain hydrocarbon, and a hydrophilic head. In an aqueous medium, such as water or saline, the tails align with each other, away from the aqueous molecules, while the heads face outward into the aqueous phase. It is this nature of the phospholipids that makes them very useful for formulating highly insoluble drugs such as those of the present invention.

The phospholipids used in the invention are selected such that their phase transition temperature is about equal to or below the body temperature or about 37° C. Representative examples of useful phospholipids include synthetic phospholipids dimyristoyl phosphatidyl choline (DMPC), dimyristoyl phosphatidyl glycerol (DMPG), dipalmitoyl phosphatidyl choline (DPPC), dipalmitoyl phosphatidyl glycerol (DPPG), distearoyl phosphatidyl choline (DSPC), or distearoyl phosphatidyl glycerol (DSPG), or a combination thereof. Other examples of phospholipids can be found in the *CRC Handbook of Lipid Bilayers* by Marsh, M.A., CRC Press (1990). When DMPC and DMPG are used in a ratio of DMPC to DMPG of about 7:3 they mimic the cell membrane.

The lipid solution is added to the DACH-Pt nitrate solution such that the weight ratio of the DACH-Pt nitrate to lipid is about 1:80 to 1:5, preferably about 1:80 to 1:10, more preferably about 1:45 to 1:25.

In some applications, it has been found desirable to add cholesterol or its hemisuccinate derivatives to the lipid complex. The cholesterol is believed to cause the bilayers to pack more closely and thereby slow the release of the drug. This approach may be particularly desirable with subcutaneous formulations where severe necrosis can result if the drug is delivered too quickly. The cholesterol is added to the phospholipid solution. The cholesterol may be used in an amount of about 0.5 to 15 parts per 100 parts phospholipid.

Any of a variety of techniques known in the art can be used to remove the solvent from the lipid-DACH-Pt dicarboxylate complex. For example, the solvent, such as the chloroform/ethanol mixture discussed above can be conveniently removed by sparging with an inert gas such as nitrogen.

The phospholipid complexes of DACH-Platinum dicarboxylate can be suspended in a pharmaceutically acceptable vehicle such as water for injection or the complex can be lyophilized with a pharmaceutically acceptable lyophilization excipient. Manitol is typically used as the excipient but other excipients which do not interact with the drug or the lipid complex may be used. Sodium or potassium phosphate, citric acid, tartaric acid, gelatin, and carbohydrates such as lactose, dextrose, dextran, hetastarch, etc. are common examples of excipients which are also believed to be useful herein. The excipients can be used alone or in combination to provide a cake of good quality which readily disperses in water upon reconstitution.

The excipients are typically added to the dispersion as solutions in water. Again, it is desirable to use concentrated solutions to minimize the amount of water for removal by lyophilization. The amount of the excipient is adjusted in a manner that is well known in the art to provide a cake which does not crack or shrink and is porous so that it readily dissolves and has a good appearance. Mannitol has been found to be useful. Mannitol is added to the dispersion as solution having a concentration of about 5 to 150 g/ml. Mannitol is added in an amount of about 1 to 100 parts by weight per 1 part phospholipid-DACH-Pt dicarboxylate complex.

After removing the solvents and adding the excipient, the dispersion is passed through a homogenizer (e.g., a Tekmar rotor/stator homogenizer, Model T25, or a microfluidics submerged jet homogenizer, Model M 11OY). As a general rule, the smaller the particle size of the dispersion, the faster the formulation can be dried during the lyophilization cycle. A dispersion having a particle size distribution ranging from about 10 to 500 nm and averaging about 250 nm has been found to be satisfactory for lyophilization. The optimum particle size may vary depending on the mode of administration.

A typical lyophilization cycle useful in accordance with the present invention is provided below. The cycle may be varied depending upon the equipment and facilities available in a manner well known in the art.

The homogenized formulation can be poured into vials of a 5 to 50 ml nominal volume. The vials are placed into a lyophilization chamber at about 5° C. The vial size will usually be selected such that each vial contains a single dosage of the phospholipid-DACH-Pt dicarboxylate. The temperature of the chamber is reduced to −30° C. over a period of one hour after which the temperature is maintained at −30 for about four hours. The pressure in the lyophilization chamber is then reduced to 200–250 microns of pressure for the remainder of the cycle. After reducing the pressure in the chamber, the temperature is ramped up to +25° C. over a period of fifteen hours and the product is held at 25° C. for five hours. The temperature then is ramped up to +40° C. over a period of 20 minutes and held at 40° C. for two hours. The lyophilized product preferably has a final moisture content of less than about 5% and typically about 1 to 2%.

For intravenous or subcutaneous administration, the complex can be reconstituted using aqueous vehicles such as water, saline or another electrolyte. The lyophilized product with the addition of water provides a colloidal dispersion of the lipid complex in an aqueous solution of the excipient. Neither the complex nor the lipids are soluble in water. A colloidal dispersion consists of at least two discrete phases. The first is a dispersed or internal phase. The second is a continuous or external phase. Systems in the colloidal state contain one or more substances that have at least one dimension in the range of 10–100Å to a few microns. See pp. 272–4 in Chapter 19, Disperse Systems, *Remington's Pharmaceutical Sciences,* 18th Edition, 1990, Mack Publishing Company, Easton, Pa. 18042. In the colloidal dispersions of the present invention the dispersed or internal phase comprises particles of the phospholipid-DACH-pt dicarboxylate complex having a particle size in the range of about 10 nm to 1000 nm. In selecting the aqueous vehicle, it is recommended to use one having a specific gravity about equal to the lipid complex (est. 1.08 g/cc) to minimize the tendency for the dispersion to separate.

The lyophilizate of the lipid complex can be reconstituted with water, saline, or another pharmaceutically acceptable aqueous diluent for intravenous administration. Upon reconstitution a dispersion is obtained which is suitable for injection. The lyophilizate can also be administered orally as an aqueous dispersion or as a paste.

For oral administration, the lyophilizate can be reconstituted to form an oral dispersion or formulated into a paste. Alternatively, the lyophilizate can be filled into a soft gelatin capsule for oral administration.

The phospholipid-DACH-Pt dicarboxylate complexes are administered in a therapeutically effective amount. Dosages for the complex are described in the literature. The drug is preferably administered as a continuous infusion over 3 to 21 days using programmable continuous infusion ambulatory pump. It is anticipated that the drug will be administered with granulocyte colony stimulating factor (GCSF).

While the phospholipid-DACH-Pt dicarboxylate complex can be lyophilized, the phospholipid-DACH-Pt dicarboxylate complexes are pharmaceutically active and typically will be formulated into a dosage form for oral, intravenous or subcutaneous administration without lyophilization. Formulation aids such as antibacterials and antioxidants can be used to enhance the stability of the complex.

Liposomes of the phospholipid complexes diaminocyclohexane dicarboxylates are prepared by adding a solution of a diaminocyclohexane platinum nitrate to the appropriate phospholipid, adding a dicarboxylic acid, evaporating the solvent used for the phospholipid to form a liposome film, adding water for injection, and homogenizing the formed liposome.

The invention will now be described in more detail with reference to the following non-limiting examples.

EXAMPLE I 20.0 g of $K_2PtCl_4$ (potassium tetrachloroplatinate), 54.2 g KI (potassium iodide) and 5.0 g of DACH (diaminocyclohexane) were dissolved in 600 mL water and the reaction allowed to proceed for 1 hour. The product, $DACH-PtI_2$ precipitated out of water.

10.8 g of $AgNO_3$ (silver nitrate) was dissolved in 170 ml of water. To this was added 17.9 g of $DACH-PtI_2$ with stirring. The reaction was allowed to proceed overnight, to yield $DACH-PtNO_3$.

To 3.1 ml of $DACH-PtNO_3$ solution, at a concentration of 65 mg/ml, was added 0.1 M sodium hydroxide until pH was between 5.5 and 5.7.

4200 mg of dimyristoyl phosphatidyl choline (DMPS) was dissolved in 8.5 ml of absolute alcohol. To this was added 1800 mg of dimyristoyl phosphatidyl glycerol (DMPG) dissolved in 5 ml of chloroform.

A 13% W/V malonic acid solution was prepared. The pH was adjusted to 5.5–5.7 with sodium hydroxide.

The lipid solution was warmed to 40–50° C., keeping the vessel covered. To this was added the $DACH-PtNO_3$ solution. The contents are stirred for 20 minutes. The cover of the vessel is then removed, and the solvents allowed to evaporate. To this is added 25 mL of 0.9% sodium chloride solution. The residual solvents are purged by sparging with nitrogen. The lipid complex suspension is q.s.'d to 50 ml. The particle size was reduced using a Tekmar homogenizer.

EXAMPLE 2

The procedure of Example 1 is repeated except that the dicarboxylic acid employed is butylmalonic acid.

Table 1 illustrates the anti-tumor activity of phospholipid complexes of DACH-platinum malonate and DACH-platinum butymalonate compared to Cisplatin and a placebo.

Having described the invention in detail and by reference to preferred embodiments thereof, it will be apparent that modifications and variations are possible without departing from the scope of the invention defined in appended claims.

TABLE 1

ANTI-TUMOR ACTIVITY OF DACH-PLATINUM COMPOUNDS AGAINST PLATINUM RESISTANT P388 CELL LINE

| Formulation | Dose mg/kg | Median Day of Death | % Increase in Length of Survival | $Log_{10}$ Change in Tumor Burden | % T/C |
|---|---|---|---|---|---|
| DACH-Pt Malonate | 60.0 | 23.5 | +80 | −2.1 | 180.7 |
| | 40.0 | 21.0 | +61 | 0 | 161.5 |
| | 27.0 | 20.0 | +53 | +0.8 | 153.8 |
| DACH-Pt Butyl Malonate | 60.0 | 21.5 | +65 | −0.4 | 165.3 |
| | 40.0 | 21.0 | +61 | 0 | 161.5 |
| | 27.0 | 20.5 | +57 | +0.4 | 157.7 |
| Cisplatin | 8.0 | 16.0 | +23 | +1.5 | 123.1 |
| | 5.3 | 15.0 | +15 | +1.5 | 115.4 |
| | 3.5 | 13.5 | +3 | +1.7 | 103.8 |
| Control (Placebo) | — | 13.0 | — | | |

Initial tumor burden = $1.0 \times 10^6$

What is claimed is:

1. A method for preparing a water soluble pharmaceutically acceptable lipid complex or liposome of a water insoluble diaminocyclohexane-platinum dicarboxylate, said method comprising reacting simultaneously diaminocyclohexane-platinum nitrate with a phospholipid and a dicarboxylic acid.

2. The method of claim 1 wherein said diaminocyclohexane-platinum dicarboxylate is a diaminocyclohexane-platinum dicarboxylate of the formula:

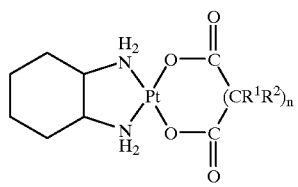

where $R^1$ and $R^2$ are the same or different and represent hydrogen, $C_1$–$C_{10}$ alkyl, $C_6$–$C_{10}$ aryl, $C_7$–$C_{18}$ alkaryl, $C_7$–$C_{10}$ aralkyl, or $R^1$ and $R^2$ may form a substituted or unsubstituted, saturated or unsaturated, 4, 5, or 6-member ring; or $R^1$ or $R^2$ may combine with $R^1$ or $R^2$ on an adjacent carbon atom to form a substituted or unsubstituted, saturated or unsaturated, 4, 5, or 6-member ring, and n is 0–10.

3. The method of claim 1 wherein said platinum dicarboxylate is a member selected from the group consisting of diaminocyclohexane-platinum oxalate, diaminocyclohexane-platinum malonate, diaminocyclohexane-platinum succinate, diaminocyclohexane-platinum glutarate, diaminocyclohexane-platinum adipate, diaminocyclohexane-platinum pimelate, diaminocyclohexane-platinum maleate, diaminocyclohexane-platinum fumerate, diaminocyclohexane-platinum phthalate, and diaminocyclohexane-platinum tartrate.

4. The method of claim 1 wherein said dicarboxylic acid is selected from the group consisting of succinic acid, glutaric acid, adipic acid, pimelic acid, maleic acid, fumaric acid, azelaic acid, suberic acid, sebasic acid, tartaric acid and phthalic acid.

5. The method of claim 3 wherein said diaminocyclohexane-platinum dicarboxylate is diaminocyclohexane-platinum malonate.

6. The method of claim 1 wherein said phospholipid is selected from the group consisting of dimyristoyl phosphatidyl choline, dimyristoyl phosphalidyl glycerol, dipalmitoyl phosphatidyl choline, distearoyl phosphatidyl glycerol, and any combination thereof.

7. The method of claim 6 wherein said phospholipid is a mixture of dimyristoyl phosphatidyl choline and dimyristoyl phosphatidyl glycerol.

8. The method of claim 7 wherein said dimyristoyl phosphatidyl choline is present in a weight ratio to said dimyristoyl phosphatidyl glycerol of about 7:3.

9. The method of claim 1 wherein said complex of said phospholipid and said water-insoluble complex of platinum dicarboxylate forms a colloidal dispersion when reconstituted with physiologically acceptable aqueous diluent.

10. The method of claim 1 wherein said complex of said phospholipid and said water-insoluble complex of platinum dicarboxylate is lyophilized.

11. The method of claim 10 wherein a pharmaceutically acceptable excipient is added to the complex.

12. The method of claim 11 wherein said excipient in mannitol.

13. The method of claim 10 wherein cholesterol or its hemissuccinate derivatives are added to said complex.

14. The method of claim 10 wherein said lipid complex forms a colloidal dispersion when reconstituted with a physiologically acceptable aqueous diluent.

* * * * *